United States Patent [19]
Lazarof

[11] Patent Number: 5,098,292
[45] Date of Patent: Mar. 24, 1992

[54] DENTAL INSTRUMENT

[76] Inventor: Sargon Lazarof, 15215 Magnolia Blvd., #126, Sherman Oaks, Calif. 91403

[21] Appl. No.: 532,853

[22] Filed: Jun. 4, 1990

Related U.S. Application Data

[63] Continuation-in-part of Ser. No. 487,837, Mar. 5, 1990, abandoned.

[51] Int. Cl.[5] .............................................. A61C 3/00
[52] U.S. Cl. .................................... 433/141; 433/229
[58] Field of Search .................. 433/141, 215, 229, 29

[56] References Cited

U.S. PATENT DOCUMENTS

| | | | |
|---|---|---|---|
| 4,445,858 | 5/1984 | Johnson | 433/229 |
| 4,673,353 | 6/1987 | Nevin | 433/90 |
| 4,818,231 | 4/1989 | Steiner et al. | 433/215 |
| 4,822,278 | 4/1989 | Oliva et al. | 433/141 |

FOREIGN PATENT DOCUMENTS

| | | | |
|---|---|---|---|
| 8606614 | 11/1986 | Fed. Rep. of Germany | 433/29 |
| 3534342 | 3/1987 | Fed. Rep. of Germany | 433/29 |

Primary Examiner—Gene Mancene
Assistant Examiner—Adriene B. Lepiane
Attorney, Agent, or Firm—James E. Brunton

[57] ABSTRACT

A dental instrument for use in filling cavities in teeth with a light activated filling compound which includes a condensing tip constructed from a plastic or glass fiber optic material. A source of light, either external to the instrument, or contained therewithin, can be selectively energized to enable controlled activation of the activator in the filling compound as the compound is being packed and shaped within the cavity by the condenser tip of the instrument. The dental instrument includes a suction cup removably connected to the tip for releasably gripping a dental overlay.

10 Claims, 3 Drawing Sheets

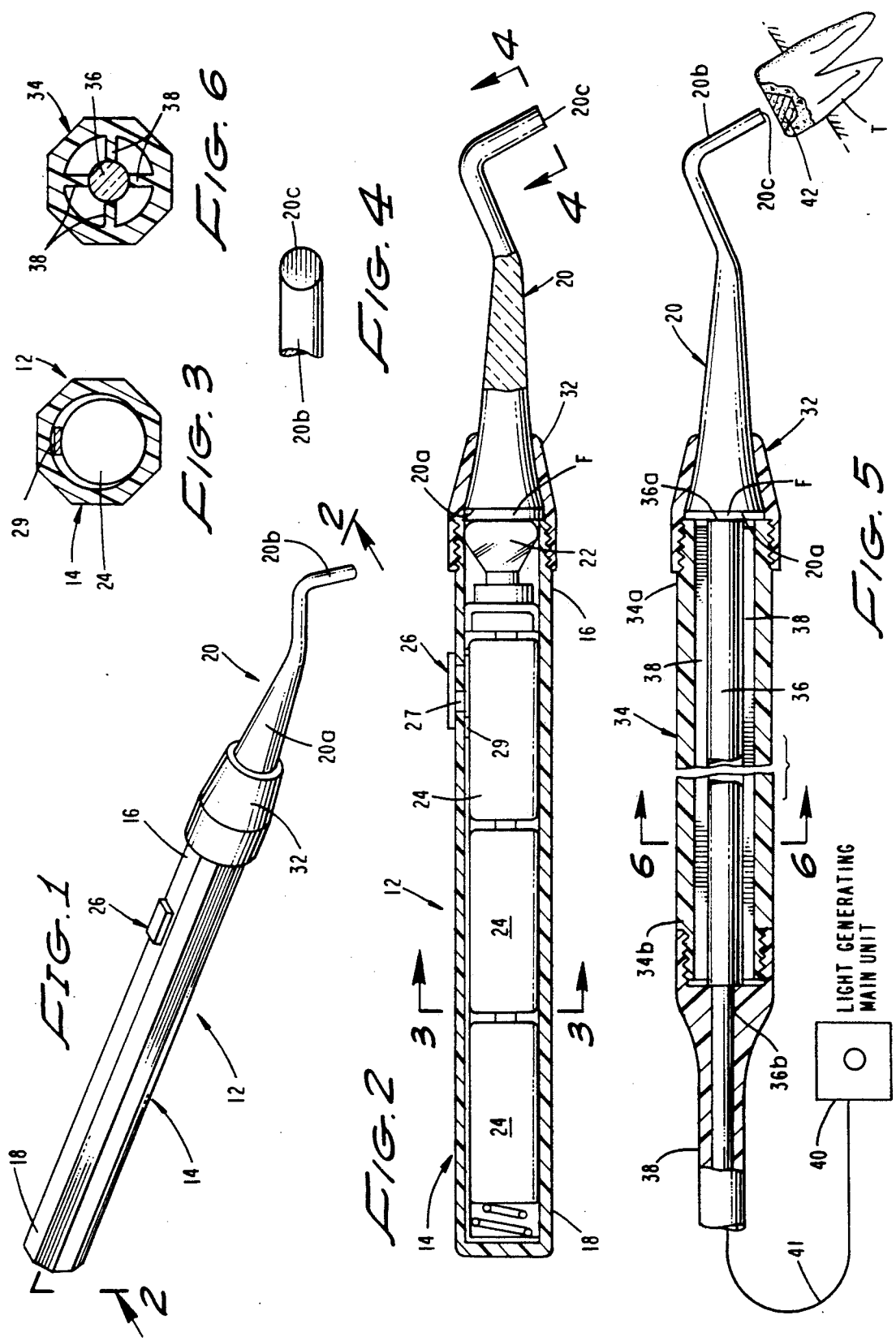

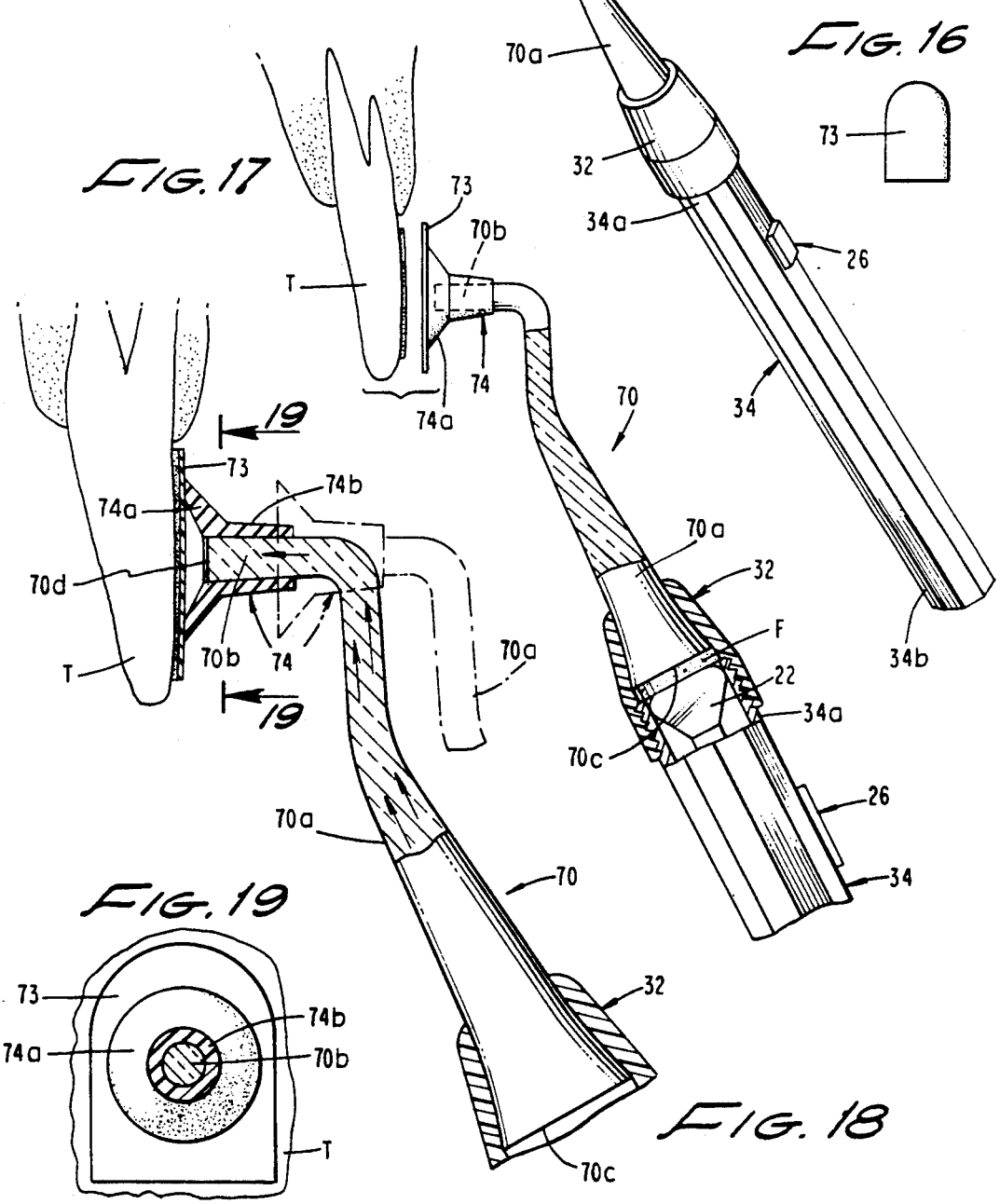

5,098,292

DENTAL INSTRUMENT

This is a continuation in part of copending application Ser. No. 07/487,837 filed Mar. 5, 1990, abandoned Jan. 8, 1991.

BACKGROUND OF THE INVENTION

1. Field of the Invention

The present invention relates generally to dental instruments. More particularly the invention concerns a hand-held instrument for use in manipulating a light-activated, cavity-filling compound.

2. Discussion of the Invention

Introduction

In filling certain types of dental cavities, a light activated filling composite or resin is used. In the past, this composite has been partially shaped and contoured by the dentist using the same instruments that are used in manipulating amalgam and like filling compounds. These instruments, called condensers, typically comprise an elongated body portion having hook-like tips at either end. The tips are of varying configurations each having differently shaped extremities including those that are bulb like in shape, frustoconical in shape and conical in shape. A complete set of instruments will typically include as many as five or six separate instruments having hook shaped extremities at either end.

The light-activated filling material, which is commercially available from several sources, remains pliable until it is exposed to a source of bright light. The bright light acts upon the activator in the composite causing it to rapidly set-up. Desirably set-up should by quite rapid and should not take place until the dentist has positioned the filling compound in precisely the correct position within the cavity. When the filling composite is correctly formed and positioned, the dentist activates the activator using a source of bright light which is inserted into the patients mouth.

In accomplishing the filling operation, the composite is usually built-up in layers with each layer being sequentially activated using a suitable source of light. Curing light apparatus is commercially available from various sources including IDE Interstate of New York, N.Y. Typical prior art curing lights comprise a body portion having a hand grip, a source of light housed within the body portion and an optical fiber, or tubular plastic, light guide extending from the forward end of the body portion.

The prior art cavity filling techniques described in the preceding paragraphs have several drawbacks. In the first place, the use of a separate, hand-held light source to activate the filling compound activator is cumbersome and time consuming. Additionally, because of the rather large size of the light guide, it is sometimes difficult to precisely focus the light beam on the filling compound. Further, when the light source is first inserted into the patients mouth, the stray light therefrom starts to prematurely act on the activator causing the filling to undesirably shrink away from the material supports used in forming or molding the filling. This, in turn, causes undesirable spacing between the filling and adjacent teeth.

As will be better appreciated from the discussion which follows, the apparatus of the present invention overcomes the drawbacks of the prior art techniques by constructing the condenser tips from a suitable plastic or glass fiber-optic material so that the tip itself can be used to accomplish the dual function of packing and shaping the filling and, as desired, simultaneously exposing the compound to a small beam of activating light. The unique configuration of the device thusly permits continued manipulation of the filling compound with the condenser tip at the same time the filling compound is curing as a result of being exposed to light.

In another form of the invention, one of the condenser tips is provided with unique suction means for releasably gripping either a dental inlay or a thin dental overlay such as a porcelain veneer of the character that can be bonded to the face of a tooth using a light activated adhesive material. Such veneers are extremely difficult to handle and emplace over the tooth using prior art techniques.

SUMMARY OF THE INVENTION

It is an object of the present invention to provide a dental instrument for use in filling cavities with a light activated filling compound in which the condensing tip of the instrument itself emits a concentrated beam of light that can be used to activate the activator in the filling compound.

It is another object of the invention to provide an instrument of the aforementioned character in which the instrument includes a hollow housing which contains a light bulb and cooperating dry cell batteries for producing the beam of light which is transmitted through the condensing tip.

Another object of the invention is to provide an instrument of the character described in the preceding paragraphs which includes a number of tips of different configuration which can be removably connected to the hollow housing.

Still another object of the invention is to provide a dental instrument having a light conducting tip that can be used with commercially available light generating units which can be interconnected with the instrument by elongated, flexible light guides.

Yet another object of the invention is to provide a dental instrument of the character described which is compact, light weight, easy to use and inexpensive to manufacture.

Still another object of the invention is to provide a dental instrument for use in gripping and strategically positioning a dental inlay or a dental overlay, or veneer, relative to a tooth using a light activated adhesive or bonding material.

BRIEF DESCRIPTION OF THE DRAWINGS

FIG. 1 is a generally perspective view of one form of the apparatus of the invention;

FIG. 2 is a cross-sectional view taken along lines 2—2 of FIG. 1;

FIG. 3 is a cross-sectional view taken along lines 3—3 of FIG. 2;

FIG. 4 is an enlarged fragmentary view taken along lines 4—4 of FIG. 2;

FIG. 5 is a cross-sectional view of an alternate form of the apparatus of the invention;

FIG. 6 is a cross-sectional view taken along line 6—6 of FIG. 5;

FIG. 15 is a generally perspective view of still another embodiment of the apparatus of the present invention for emplacing dental overlays;

FIG. 16 is a plan view of a typical dental overlay;

FIG. 17 is a side elevational view partly in cross-section of the apparatus shown in FIG. 15;

FIG. 18 is an enlarged side elevational view partly in section showing the tool being used to emplace the dental overlay over the face of a tooth; and FIG. 19 is a cross-sectional view taken along lines 19—19 of FIG. 18.

FIG. 20 is a fragmentary view of another form of tip for releasably gripping and strategically positioning dental inlays.

DESCRIPTION OF THE INVENTION

Figure 7:
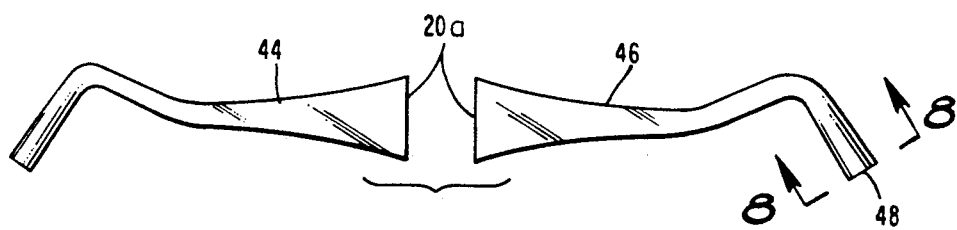
FIG. 7 illustrates a pair of differently formed operating tips which can be interconnected with the body portion of the apparatus.
Figure 8:
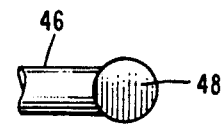
FIG. 8 is an enlarged fragmentary view taken along line 8—8 of FIG. 7.

Referring to the drawings and particularly to FIGS. 1 and 2, the dental instrument for use in filling cavities with a light-activated filling compound is generally designated by the numeral 12. In one embodiment of the invention, the instrument comprises an elongated hollow body 14 having first and second ends 16 and 18 and a condenser tip 20 removably connected to body 14 proximate the first end 16 thereof.

Tip 20 includes a first portion 20a disposed in coaxial alignment with body portion 14 and a second portion 20b extending angularly downwardly with respect to the longitudinal axis of body 14. Tip 20 is constructed from a material that will conduct a beam of light from the first end of the tip to the extremity of the second end of the tip 20b. The material used in the construction of tip 20 can be any suitable plastic or glass fiber-optic or beam guide material that will function to conduct the beam of light from the first position of the tip toward the extremity of tip 20b. Suitable materials for construction of the tip are available from Corning Glass Works of Corning, N.Y. Various acrylic plastics can also be used to form the tip. Also forming apart of the dental instrument of the invention is a light beam generating means operably associated with tip 20 for generating a beam of light and directing it toward the first end 20a of the tip 20.

In the form of the invention illustrated in FIGS. 1 and 2, the light-beam generating means comprises a light bulb 22 mounted within hollow body 14 in close proximity with end 20a of tip 20 and a plurality of dry cell batteries 24 mounted within hollow body 14, batteries 24 are operably associated with bulb 22 via an appropriate switch means shown in FIG. 2 as a mechanical switch 26 of a simple, well-known construction mounted on body 14. As best seen by referring to FIG. 3, hollow body 14 is generally octagonal in shape and mechanical switch 26 is slidably mounted within a slot provided on the exterior surface of the hollow body. Movement of switch 26 from a first position, wherein a contact 27 on the switch is spaced from a contact 29 in engagement with first battery 24, to a second position wherein contacts 27 and 29 engage will energize the light bulb causing a beam of light to be directed toward end 20a of tip 20. This beam of light will be guided through the tip and will exit the tip through surface 20c (FIG. 4) provided on tip end 20b. As best seen in FIG. 2, body 14 is externally threaded at its forward end to threadably receive an internally threaded tubular connector member 32 that holds tip 20 in proper position with end 20a disposed in close proximity with bulb 22. Removal of connector member 32 permits replacement of bulb 22 and batteries 24 as required.

Turning now to FIG. 5, an alternate embodiment of the apparatus of the invention is there illustrated. This embodiment is similar in many respects to the embodiment shown in FIGS. 1 through 4 and like numerals used to identify like components. This second form of the invention comprises a hollow body 34 having an externally threaded first end 34a and an externally threaded second end 34b. A tip 20 of identical construction to that previously described is removably interconnected to body 34 by means of connector 32. Tip 20 can be constructed of any suitable plastic or glass fiber optic or beam-guide material that will function to conduct a beam of light toward the extremity 20b of tip 20. If desired, tip 20 can be constructed with a central portion comprising a multiplicity of thin glass fiber optic strands which conduct a beam of light from end 20a thereof to end 20b in a manner that the beam of light is emitted from surface 20c. The central light guide portion, or core, of fiber optic strands can be surrounded by a moldable plastic material formed in the shape of a tip 20 of the character illustrated in FIG. 5.

In the form of the invention shown in FIG. 5, the light beam generating means, rather than comprising a light bulb energized by a plurality of batteries, comprises a generally tubular shaped member 36 which is disposed internally of housing 34 and is maintained axially aligned therewith by radially inwardly extending support webs 38 (FIG. 6). Member 36 has a first end 36a disposed in close engagement with first end 20a of tip 20 and a second end 36b disposed proximate end 34b of housing 34. Member 36 can be constructed from any suitable plastic or glass fiber optic or beam guide material that will function to conduct a beam of light from extremity 36b thereof to extremity 36a thereof.

Threadably connected at end 34b of housing 34 is an internally threaded adapter 38 which forms a part of a light guide which may be interconnected with a commercially available light beam generating unit of the character offered for sale by IDE Interstate under Catalog No. 440592. This light generating main unit, designated in the drawings by the numeral 40, produces a bright beam of light which is conducted from unit 40 to connector unit 38 by means of a flexible light guide generally designated in the drawings by the numeral 40. When the light generating main unit is energized, a light beam will be transmitted through the light guide to connector 38 and thence through beam guide 36. The light beam emitted from end 36a of beam guide 36 will then be transmitted from end 20a to end 20b of tip 20 and will exit from surface 20c in a sharply focused beam of light.

As indicated in FIG. 5, the beam of light emanating from surface 20c can be precisely directed toward the filling compound 42 which is being used to fill the cavity in tooth T. As previously discussed, tip 20 can be used in the same manner as conventional prior art condenser units to pack and shape the filling material 42.

When the filling material is in the desired configuration, the light generating main unit can be activated causing a beam of light to flow through the unit and emanate from surface 20c. This beam of light will activate the activator in the filling compound 42 causing it to begin to set up. As the material sets up, tip 20 can continue to be used to finally pack and shape the filling material 42 within the cavity in the tooth. Filling compounds suitable for use with the apparatus of the invention are commercially available from various sources, including Lee Pharmaceuticals of South El Monte, Calif. and Dentsply International, Inc. of Milford, Del. In both forms of the invention shown in the drawings, a filter means, provided in the form of a filter disk F, is disposed between the tip and light source for properly filtering the light for maximum efficiency for the particular filling compound used.

Referring now to FIGS. 7 through 14, various configurations of tips usable with the apparatus of either the first or second previously described forms of the invention. The tips 44 and 46 shown in FIG. 7 are of similar construction to tip 20 each tip terminating in a flat generally circular shaped surface 48. The diameter of tip end 48 can be of various sizes as illustrated in the drawings.

Figure 9:
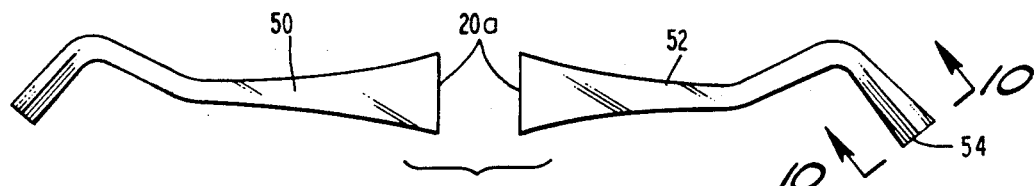
FIG. 9 is a view of another pair of operating tips connectable to the body portion of the device.
Figure 10:
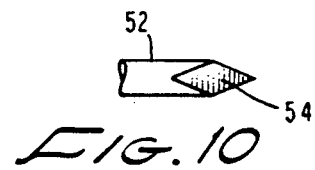
FIG. 10 is a fragmentary view taken along lines 10—10 of FIG. 9.

The tips 50 and 52 shown in FIG. 9 are of similar construction to tip 20 but terminate in a generally diamond shape end surface 54. Once again, the size of the diamond shape end portion can vary in the manner shown in the drawings.

Figure 11:
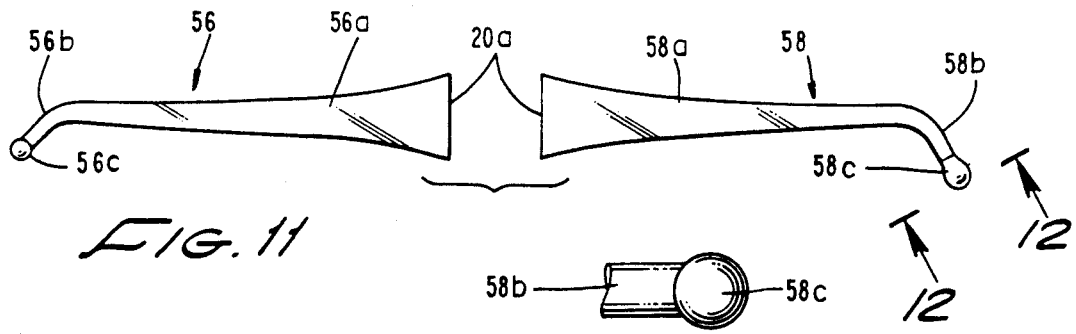
FIG. 11 illustrates still another pair of operating tips usable with the device.
Figure 12:
FIG. 12 is an enlarged fragmentary view taken along lines 12—12 of FIG. 11.

In FIG. 11, tips 56 and 58 are shown as comprising an elongated, narrow, generally horizontally extending portion 56a and 58a terminating in a downwardly extending tip portion 56b and 58b. Tips 56b and 58b terminate in a generally bulb-like configuration 56c and 58c. The size of the tips, 56c and 58c, can vary in the manner shown in the drawings.

Figure 13:
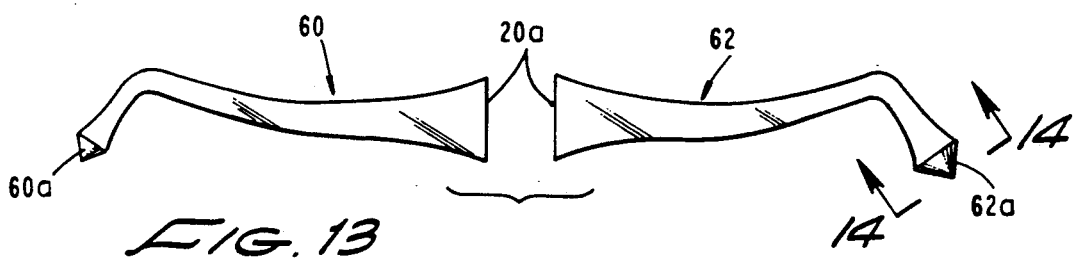
FIG. 13 illustrates yet another pair of operating tips.
Figure 14:
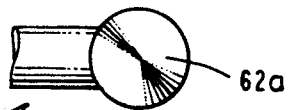
FIG. 14 is an enlarged fragmentary view taken along lines 14—14 of FIG. 13.

Turning to FIGS. 13 and 14, yet another pair of condenser tips usable with either of the previously described embodiments of the invention is there shown. These tips designated by the numerals 60 and 62 are of similar construction to the tips shown in FIGS. 9 and 10 but terminate in a generally conical shape end 60a and 62a, respectively. Once again, the size of the conical shaped ends of the tips can vary in the manner shown in FIG. 13.

It is apparent that through the use of the single instrument of the present invention and the selective interconnection of the variously configured tips shown in FIGS. 7 through 14 permit the one instrument to substitute for a prior art set comprising several separate instruments. Using the single hand-held housing with the appropriately shaped tip, the filling material can be packed and shaped using the one instrument in exactly the same manner as using prior art sets of several instruments.

Referring to FIG. 15, another alternate embodiment of the apparatus of the invention is there illustrated. This embodiment is similar in many respects to the embodiment shown in FIGS. 1 through 4 and like numerals used to identify like components. This second form of the invention also comprises a hollow body 34 having an externally threaded first end 34a and an externally threaded second end 34b. A tip assembly 70 of similar, but slightly different construction than tip 20 as previously described, is removably interconnected to body 34 by means of connector 32 (FIG. 17). Tip assembly 70 includes a tip portion 70a that can be constructed of any suitable plastic or glass fiber optic or beam-guide material that will function to conduct a beam of light toward its extremity 70b. As before, tip 70a can be constructed with a central portion comprising a multiplicity of thin glass fiber optic strands which conduct a beam of light from end 70c thereof to end 70b in a manner that the beam of light is emitted from surface 70d (FIG. 18). Also forming a part of tip assembly 70 is a suction means for applying suction to one face of a dental overlay 73 of the character shown in FIG. 16.

In the form of the invention shown in FIGS. 15 through 19, the suction means is provided in the form of a small suction cup 74 having a peripheral portion 74a adapted to releasably grip the overly and an integrally formed, generally tabular portion 74b adapted to closely fit over end 70b of tip 70a to hold the suction cup in proper position.

In using the apparatus of this latest form of the invention, the overlay 73 is first picked up using the suction cup in the manner illustrated in FIG. 15. The front surface of the tooth is then coated with light activated adhesive and the overlay is moved toward tooth T in the manner shown in FIG. 17. Next, the overlay is firmly pressed against the tooth as shown in FIG. 18. When the overlay is precisely positioned against the tooth in the desired orientation and location, light energizing switch 26 is moved to the second position to energize light bulb 22. Tip 70 will then conduct the light toward surface 70d of the tip causing activation of the adhesive. After the adhesive is completely set-up, the suction cup is separated from the overlay in the manner shown by the phantom lines in FIG. 18. This procedure uniquely permits precise positioning of the overlay during the critical step of activating the adhesive and prevents any undesirable movement of the overly relative to the tooth prior to a secure bonding of the overlay to the tooth. The device of this form of the invention can also be used to releasably grip and then strategically position dental inlays as well as dental overlays or veneers.

It is to be understood that the form of the apparatus shown in FIG. 5, that is the apparatus which uses an external light source, can also be used in conjunction with tip assembly 70.

Turning to FIG. 20, there is illustrated the use of a tip 80 of the same character shown in FIG. 7 for gripping and strategically positioning a dental inlay 82 within a cavity formed in a tooth. In using tip 80, an inlay gripping means, shown here as a small mass 84 of a sticky substance, such as gum or adhesive, is affixed to the end of the tip. The tip can then be used to pick up the inlay 82 and transfer it to the cavity. The sticky substance is then removed and the tip is used to pack and form the inlay. This done, the light source is energized in the manner previously described to activate the adhesive which holds the inlay in place within the cavity.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A dental instrument for use in filling cavities with a light activated filling compound, comprising:

(a) an elongated body having first and second ends;

(b) a plurality of tips adapted to be removably connected to said body, each said tip having a first portion in substantial coaxial alignment with said elongated body and an integral second portion extending angularly with respect to the longitudinal axis of said elongated body said second portion terminating in a fixed extremity having a continuous, closed surface for packing and shaping the filling compound, said tip being constructed of a material that will conduct a beam of light from said first end to said second end; and (c) a light beam generating means operably associated with said top for generating a beam of light and directing it toward said first end of said tip.

2. A dental instrument as defined in claim 1 in which said light-beam generating means comprises a light source operably associated with tip.

3. A dental instrument as defined in claim 2 in which said light beam generating means comprises:
   (a) a light bulb carried by said body;
   (b) at least one battery carried by said body; and
   (c) switch means carried by said body for operably interconnecting said light bulb and said battery.

4. A dental instrument as defined in claim 2 in which said light source is remotely located and in which said generating means comprises conductor means for conducting a beam of light from said remotely located light source and said first end of said tip.

5. A dental instrument as defined in claim 4 in which said conductor means comprises an elongated cylindrical member mounted internally of said elongated body.

6. A dental instrument as defined in claim 1 further including a suction cup removably connected to said second portion of one of said tips for releasably engaging a dental overlay.

7. A dental instrument for use in filling cavities with a light activated compound and for applying a dental overlay to a tooth using a light-activated adhesive comprising
   (a) an elongated body;
   (b) a plurality of tips connected to said body, each said tip having first and second ends and terminating in a fixed extremity defining a solid surface for packing and shaping the light activated compound, said tips being constructed of a material that will conduct a beam of light between said first and second ends;
   (c) a suction cup removably connected proximate said fixed extremity of a selected tip for releasably gripping the dental overlay; and
   (d) a light beam generating means operably associated with each said tip for generating a beam of light and directing said beam of light between said first and second ends of thereof.

8. A dental instrument as defined in claim 7 in which said light beam generating means comprises a remotely located light source operably associated with said tip.

9. A dental instrument as defined in claim 7 in which said elongated body is provided with an elongated chamber and in which said light beam generating means comprises:
   (a) at least one dry cell battery carried within said elongated chamber; and
   (b) a light bulb disposed proximate said first end of said tip, said light bulb being operably interconnected with said battery.

10. A dental instrument as defined in claim 7 in which said suction cup comprises a cup portion having a peripheral surface adapted to sealably engaged the dental overlay for interconnecting said suction cup portion to said second end of said tip.

* * * * *